United States Patent [19]

Ellingsen et al.

[11] Patent Number: 5,169,634
[45] Date of Patent: Dec. 8, 1992

[54] PHARMACEUTICAL DOSAGE FORM FOR THE MEDICATION OF FISH

[75] Inventors: Odd F. Ellingsen, Trollasen; Kjell E. Nordby, Oslo; Knut E. Rasmussen, Asker, all of Norway

[73] Assignee: Apothe Kernes Laboratorium A.S., Oslo, Norway

[21] Appl. No.: 829,514

[22] Filed: Jan. 30, 1992

Related U.S. Application Data

[63] Continuation of Ser. No. 613,576, filed as PCT/NO89/00059, Jun. 14, 1989.

[30] Foreign Application Priority Data

Jun. 15, 1988 [NO] Norway .................................. 882653

[51] Int. Cl.$^5$ ............................................. A23K 1/165
[52] U.S. Cl. .................................................... 424/442
[58] Field of Search .......................... 424/442; 514/300

[56] References Cited

U.S. PATENT DOCUMENTS

| | | | |
|---|---|---|---|
| 2,358,320 | 9/1944 | Eisaman | 424/442 |
| 3,993,746 | 11/1976 | Beigler et al. | 424/78 |
| 4,390,260 | 9/1985 | Beigler et al. | 424/84 |
| 4,413,014 | 11/1983 | Melancon | 426/1 |
| 4,861,586 | 8/1989 | Schneider et al. | 424/84 |

FOREIGN PATENT DOCUMENTS

| | | |
|---|---|---|
| 0240826 | 10/1987 | European Pat. Off. |
| 0246910 | 11/1987 | European Pat. Off. |
| 2423608 | 1/1975 | Fed. Rep. of Germany |
| 3224365 | 1/1984 | Fed. Rep. of Germany |
| 167022 | 12/1975 | New Zealand |
| 195377 | 7/1984 | New Zealand |
| 198533 | 12/1984 | New Zealand |
| 217387 | 8/1989 | New Zealand |
| 215757 | 12/1989 | New Zealand |
| 218589 | 12/1989 | New Zealand |
| 222557 | 12/1989 | New Zealand |
| 224529 | 2/1990 | New Zealand |
| WO85/05015 | 1/1984 | PCT Int'l Appl. |
| 1113918 | 12/1985 | U.S.S.R. |

*Primary Examiner*—Frederick E. Waddell
*Assistant Examiner*—Gregory Hook
*Attorney, Agent, or Firm*—Seidel, Gonda, Lavorgna & Monaco

[57] ABSTRACT

A pharmaceutical dosage form for administration of medicament to fish has an outer layer of animal or vegetable material surrounding at least one inner chamber containing one or more biologically active agents. The outer layer, which is composed of animal and/or vegetable material and/or an aqueous extract from marine materials, and an optional binder, is substantially impermeable to water and the medicament. The chamber is filled with the active agent in a viscous pharmaceutical formulation to improve the bioavailability and stability of the active agent. The chamber may be partly filled with gas. The buoyancy of the dosage form in water is manipulable by adjusting the volume and contents of the inner chamber.

12 Claims, 5 Drawing Sheets

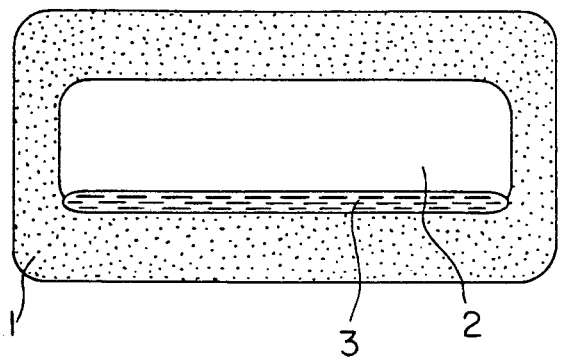
F I G. 1
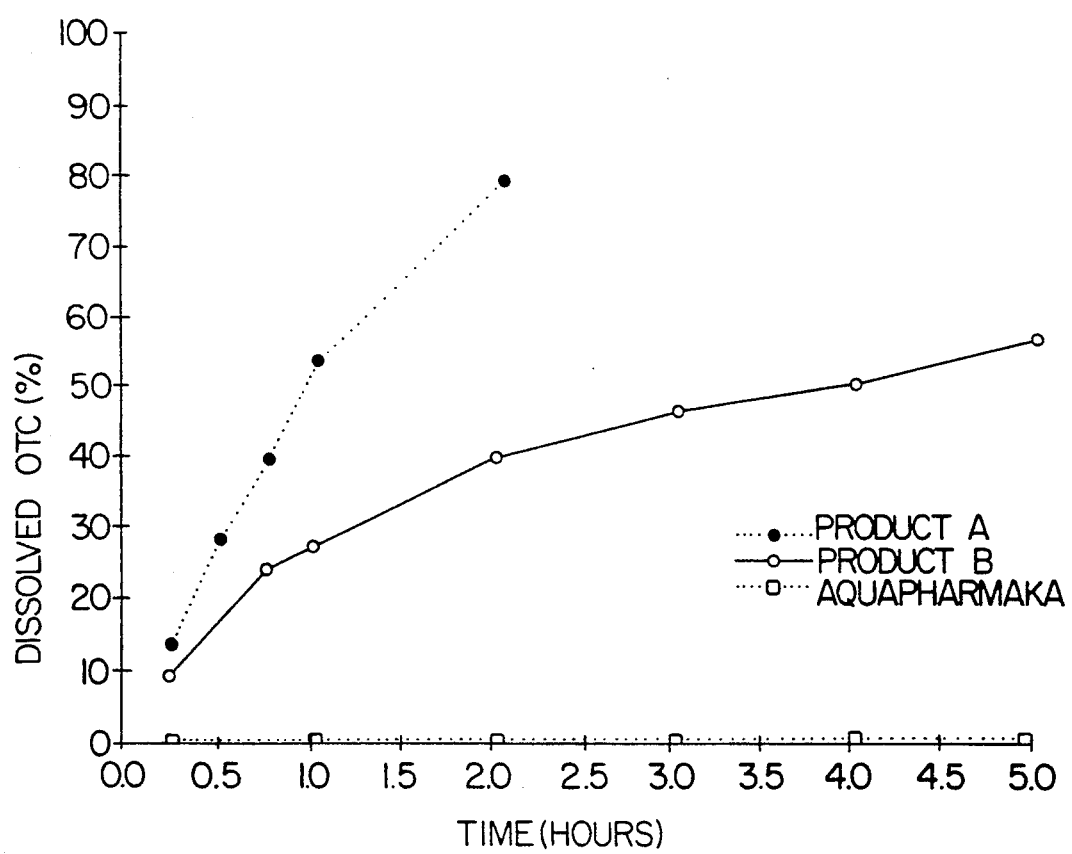
F I G. 2

PHARMACEUTICAL DOSAGE FORM FOR THE MEDICATION OF FISH

This is a continuation of co-pending application Ser. No. 07/613,576 filed as PCT/NO89/00059, Jun. 14, 1989, now abandoned.

FIELD OF THE INVENTION

The present invention relates to the medication of fish, and in particular to a pharmaceutical dosage form therefor.

BACKGROUND OF THE INVENTION

Numerous problems are encountered in the feeding and medicating of fish. The behavior of fish at feeding is strongly influenced by prevailing conditions at the time of feeding. Such conditions include, for example, the temperature and acidity of the water; the level of dissolved nitrates and other substances in the water; the consistency and nature of the feed, e.g., hardness, taste and flotation properties; and the health state of the fish.

Known methods of fish medication include mixing medication with fish feed. Oral administration of medicines in this manner is complicated by the tendency of most medicaments to adversely affect the taste of the feed, which becomes unacceptable to the fish. Moreover, many types of known medicated feeds are prepared in the form of pellets. Medication, and antibiotics in particular, are mixed into dry food pellets without considering the pharmaceutical aspects of drug formulation, and sold as medicated pellets for fish. The pellets are characterized by poor bioavailability of the drug substance. The pellets also sink too rapidly for ingestion by the fish. The unused portion of the medicated feed represents a source of pollution in the fish farming facility, or other environment in which the medicated feed is released.

Many fish medicines are toxic, in high concentrations. Thus, handling the feed coated with medication may be harmful to humans. Fish breeders utilizing "soft" medicated feed generally prepare the same by mixing the medication with available feed materials. Such non-industrial mixing methods fail to permit adequate control over the concentration of active material in the feed. The mixing of large quantities of biologically active materials poses a health hazard for the fish breeder. The dispersion of the medication in water, from disintegrated feed or carrier, represents an additional source of pollution or direct harm to the environment.

Several methods have been proposed to make fish feed more acceptable or more easily accessible to fish. U.S. Pat. No. 4,413,014 discloses a food or bait material comprising a solid edible porous corn material saturated with a fish attractant liquid. The article is produced with a core of feed solid material, and may also be coated with a solid edible material.

U.S. Pat. Nos. 4,393,087 and 2,358,320 disclose methods for rendering fish feed more available to fish by influencing the feed's flotation properties. The firstmentioned patent discloses a process for producing floating feed pellets formed from a combination of fish meal and a protein-containing material, including expanded grain particles to render the pellets buoyant in water. U.S. Pat. No. 2,358,320 describes a fish feed consisting of a material that is denser than water, but which is rendered buoyant in water by forming the material into hollow pellets.

International Patent Application No. WO 85/05015 describes a method of rendering feed more attractive to fish. Pellets having a soft consistency are formed with a surface coating of a hardenable gel material, such as, alginate, guar gum, tragacanth gum, pectin or gelatin. The pellets may be imparted with varying flotation properties.

While the above-described references are interesting, they do not disclose dosage forms containing medicines; nor do any of the references address the problems which may arise in the oral administration of medicaments to fish.

"Oxytetracycline Vet. EWOS IOG/KG Medicine Pellet for Fish 9P", manufactured by EWOS AB, Södertälje, Sweden, (hereinafter "Product A") is prepared by mixing medication into fish feed according to pressure-pelleting techniques, followed by drying. Medicated feeds prepared according to such techniques are not buoyant, but rather sink rapidly, reducing the change of uptake by fish, and increasing the pollution of the environment. Furthermore, such feeds offer little control over the quantity of medicament actually assimilated by the fish, and suffer from poor absorption and bioavailability of the medicament.

"Skretting Tess Medicine Pellet for Fish (7.5g OTC/Kg)", manufactured by T. Skretting A/S, Stavanger, Norway, (hereinafter "Product B") is produced by applying a coating of medication to the surface of dry fish food. The medication is suspended in oil and sprayed onto the surface of the feed. The larger part of the medication remains on the surface of the feed pellet, while the balance is absorbed into the feed, together with the oil. Medicated feeds prepared in this manner suffer from being unpalatable to fish by virtue of the taste or smell of the medication deposited on the feed surface. The degree of utilization by the fish is particularly poor where the medication has a characteristic or penetrating taste, as in the sulfonamides or nifurazolidone, for example. Since the medication is present mainly on the surface of the feed, the fish breeder or worker will be exposed thereto. Moreover, the accuracy of the dosing is inherently poor in such feeds.

It is thus an object of the present invention to provide a dosage form for medicating fish, which eliminates the above mentioned disadvantages, while at the same time permitting effective delivery of medication to fish.

SUMMARY OF THE INVENTION

To achieve these goals, a pharmaceutical dosage form for administration of a biologically active agent to fish is provided.

The dosage form comprises an outer layer substantially impermeable to water and the active agent. The outer layer comprises at least one material selected from the group of animal material, vegetable material and an aqueous extract from marine materials. At least one chamber containing at least one active agent is surrounded by the outer layer.

The animal material preferably comprises fish meal. The outer layer further preferably contains a binder for the animal or vegetable material.

The inner chamber is, by co-extrusion, partially filled with a formulation of the biologically active agent in a viscous suspension comprising adjuvants, absorption enhancers or carriers, to improve the bioavailability and stability of the active agent. The inner chamber may also be partly filled with a fluid, preferably a gas or gas composition such as air. Inert gases such as nitrogen may be employed. The buoyancy of the dosage form in water may be manipulated by adjusting the volume of the inner chambers. Buoyancy may also be manipulated in the selection of fluids utilized to fill the chamber. Thus, the chamber effectively functions as a means for selectively manipulating the buoyancy of the dosage form in water.

A method for treating diseased fish, and a method for prophylactic treatment of fish, are provided, by administering at least one biologically active agent to the fish in the form of a pharmaceutical dosage form according to the invention.

By "biologically active agent" or "active agent" is meant not only pharmaceutical substances for the treatment or prevention of disorders or diseases which may afflict fish, but also other bio-affecting materials which find utility in fish farming or in the care of fish, such as, for example, growth stimulating or growth regulating substances. Moreover, it is contemplated that one or more biologically active agents may be contained in the dosage form of the present invention. Hence, unless indicated otherwise, reference to "a biologically active agent" in the singular herein specification and appended claims is understood to also include the containment of plural active agents in the dosage form.

By "substantially impermeable to water and the active agent" is meant that under conditions of normal use, the outer layer of the dosage form resists the passage of water into the chamber, and the release of active agent from the chamber, as long as the outer layer remains substantially intact.

By "animal material" is meant any portion of the body or remains of any animal, which portion may be prepared in a form suitable for forming the outer layer of the instant dosage form. Such material, in its most basic form, comprises cells or cellular components from unicellular or multicellular members of the animal kingdom. In particular, the animal material may include material derived from fish or other aquatic animals.

By "vegetable material" is meant any portion of a plant which may be prepared in a form suitable for forming the outer layer of the instant dosage form. In its most basic form, such material comprise cells or cellular components from unicellular or multicellular members of the plant kingdom.

By "fish meal" is meant a feed product formed by the processing or raw marine materials. According to the typical fish meal manufacturing process, raw marine materials such as those hereinafter described, are optionally cooked with water and pressed into the form of cakes, known as press cakes. The liquid material pressed out of the cakes comprises an oil component and an aqueous component or "press water". The press water is recombined with the press cake as by mixing, and the water is evaporated. The resulting products comprises one form of "fish meal".

By "aqueous extract from marine materials" or "marine materials aqueous extract" is meant the aqueous extract from marine materials such as herring, blue whiting, octopus waste (i.e., the portion of the animal not used for human consumption), fist waste, shrimp waste, krill, and the like, in addition to the aqueous press water which is a by product of the production of fish meal. The press water, which may be literally translated from the Norwegian language as "glue water" due to its properties as a binder, comprises an aqueous extract of the water soluble compounds of raw marine materials. Such compounds include, for example, proteins, peptides, amino acids and nucleotides. These serve as taste components which act as attractants and stimulants for the feeding of farmed fish. In addition to its attractant and stimulant properties, the extract also exhibits excellent binding properties.

Included with the scope of the term "aqueous extract from marine materials" or "marine materials aqueous extract" is not only the extract per se, as it is produced as a by product from the fish meal manufacturing process, but also included are further refined products based on the aqueous extract. For example, it is known that the aqueous extract from marine materials may be subjected to enzymatic hydrolysis to break down proteins and peptides, in order to provide a higher concentration of amino acids, and an improved taste. Furthermore, the aqueous extract may be enriched with taste components in solid or concentrated solution form.

BRIEF DESCRIPTION OF THE FIGURES

FIG. 1 illustrates an embodiment of the dosage form of the invention in cross-section.

FIG. 2 compares the release of oxytetracyclineHCl (hereinafter "OTC-HCl") to seawater at 4° C. from the commercially available medicated feed pellets Product A and Product B, respectively, and the release of OTC-HCl from a dosage form (designated "AQUAPHARMAKA") prepared according to the present invention.

DETAILED DESCRIPTION OF THE INVENTION

Figure 3:
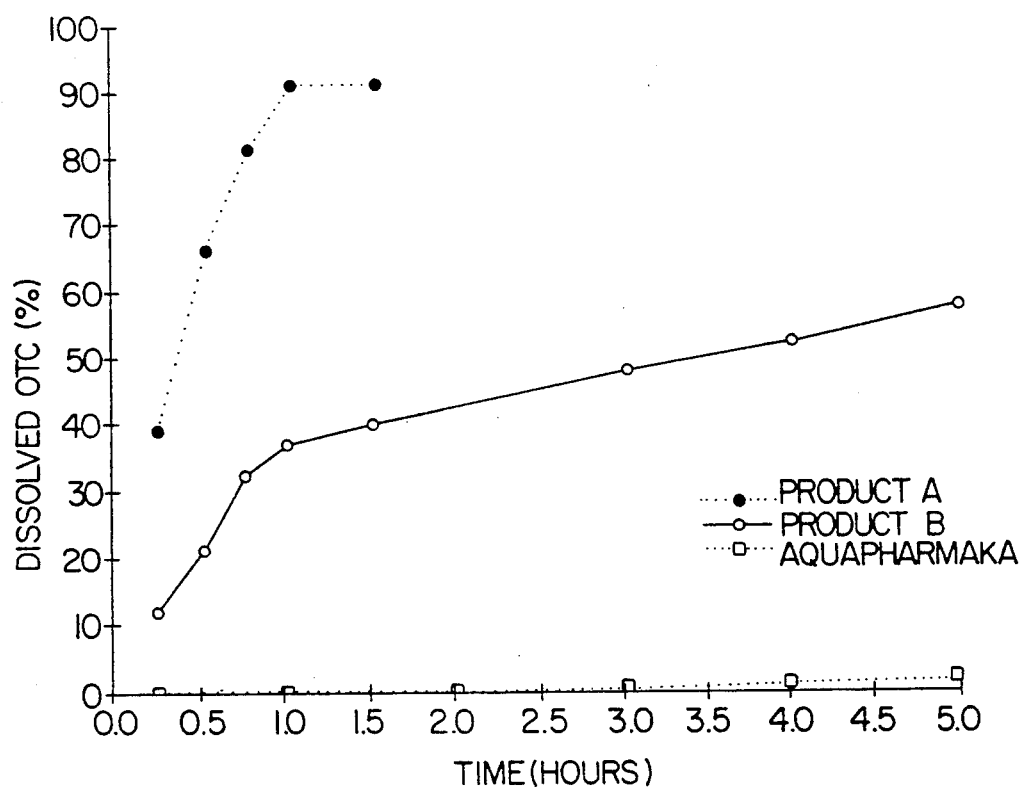
FIG. 3 compares the release rates of the same dosage forms, but at a water temperature of 18° C.

Referring to FIG. 1, a dosage form according to the present invention is shown having an outer layer 1 and an inner chamber 2, containing active agent 3. The medicament is optionally contained in a carrier material.

Thus, in one embodiment of the invention, the dosage form is in the shape of a "cushion". The outer layer contains, an animal or vegetable material (preferably a fish meal) and/or aqueous extract from marine materials, optional concentrated taste components and optional binder. The components of the outer layer may be selected to ensure a taste and smell for the product which stimulates feeding. The layer effectively masks the taste of the active agent contained in the chamber. For example, the outer layer may comprise, by weight, 60% micronized fish meal produced by low temperature technology from fresh fish, such as winter herring, blue whiting, capeline, etc.; 35% by weight of an aqueous extract from marine materials such as herring, blue whiting, octopus waste (i.e, the portion of the animal not used for human consumption), fish waste, shrimp waste, krill, etc. in addition to the aqueous press water which is a by-product of the production of fish meal; and about 5% by weight of a binder. The binder may comprise one or more modified starch derivatives, such as, but not limited to, modified hydroxypropyl-distarch-phosphate.

Vegetable materials which may comprise the outer layer or a portion thereof include, for example, soy meal, potato starch and starch derivatives, wheat flour, lactose, and the like.

The marine materials aqueous extract advantageously has a dry matter content of about 30-40% by weight, and is preferably produced by aqueous extraction of marine materials. The aqueous extract may be present in solubilized form, as well as in dry form.

In the outer layer of the dosage form, the binder may be present in concentrations within the range of from about 5% to about 20%, preferably about 10%, based on the weight of the dosage form. The binder favorably interacts with the binding properties of the marine materials aqueous extract, so as to increase the physical strength of the outer layer.

The dosage form may be produced by co-extruding the outer layer with the material in the chamber. The outer layer is advantageously extruded with a water content of about 15-30%, preferably about 20%, and is then dried to a water content of about 10-20%, preferably 13%.

The volume of the chamber 2, may comprise, for example, a volume equal to 10 times the volume of the medicament 3. Other volume ratios will be evident to those skilled in the art. The chamber 2 may be filled with up to about 10-20% by weight of the co-extruded medication-containing mass based upon the weight of the dosage form. In a preferred embodiment of the invention, the ratio between the outer and inner diameter of the dosage form is about 2:1.

As mentioned previously, the dosage form of the invention is advantageously manufactured by co-extruding the outer layer around the inner material, that is, the material containing the active agent. The dosage form is shaped with one or more chambers to provide the buoyancy properties. With this construction, the dosage form exhibits not only excellent storage stability, but is stable in water. By virtue of the impermeability of the outer layer, the active agent is not prematurely released into the surrounding water. The active component remains chemically stable within the dosage form. The animal or vegetable material forming the principal component of the outer layer is readily digestible in the stomach of the fish, so that the active agent in the chamber is released to the digestive tract of the fish.

In addition to containing the active agent, the chamber may be filled with a fluid, preferably a gas or a gas mixture, such as air. Inert gases such as nitrogen may be employed to inhibit oxidation of the medicament in the inner chamber.

The active agent may comprise any biologically active agent which has utility in the care or farming of fish. Such agents include, for example, antibacterial or antiparasitic compounds such as the tetracyclines, preferably oxytetracycline ("OTC") or a salt thereof; flumequine; and oxolinic acid. The foregoing are mentioned by way of illustration, and not by limitation. Substances other than medicines may also be added to the chamber of the dosage form. Such substances include, for example, vitamins, minerals, and the like.

According to the invention, there may be envisioned numerous embodiments for the active material-containing portion 3 of the dosage form. For example, the active agent may be present in pure or concentrated form, or may be diluted with one or more adjuvants or carriers to improve the bioavailability and stability of the agent. According to a preferred embodiment, the biologically active agent contained within the chamber is formed by suspending or dissolving the active agent in an emulsion or suspension, such as an emulsion of a fat material. Fat material suited for such emulsions include fats or lipids which are liquid at about 0° C. The active agent may be suspended, emulsified, dispersed or dissolved in the emulsion. Active agents which might otherwise be readily hydrolyzed are thus stabilized. Other additives or carriers may also be included with the active agent, provided that they are extrudable. For example, the extrudable carrier may comprise an antioxidant to prevent oxidation of the active agent during storage of the dosage form.

The active agent may be contained in a carrier comprising a gel matrix formed from an aqueous gelforming material. Such materials include for example, sodium carboxymethyl cellulose, microcrystalline cellulose; polyvinylpyrrolidone; carboxypolymethylene, for example, Carbopol ®940, available from B. F. Goodrich; and the like. Such a carrier is particularly useful for preparing flumequine-containing dosage forms according to the present invention having improve absorption of flumequine.

The following comparative experiments were conducted to further illustrate the advantages of the dosage form of the invention over the commercially available medicated fish feed pellets Product A and Product B. In particular, it is noted that the dosage form of the present invention resists premature release of the active agent into the surrounding environment before ingestion by fish. Thus, unlike the prior art products, the dosage form of the present invention avoids polluting the environment with the active agent.

EXAMPLE 1

Active Agent Release Studies—OTC

Six units of each of Product A, Product B, and a dosage form according to the present invention designated "AQUAPHARMAKA", all containing OTC-HCl, were placed in a glass beaker containing 800 ml of fresh seawater. The concentration of OTC. in each of the tested products was 1%, and the weight of OTC. per dosage unit was about 0.8 grams. The release of OTC. from the pellets into the surrounding seawater was determined at two different water temperatures, 4° C. (FIG. 2) and 18° C. (FIG. 3). Water samples of 5 ml were taken from the beaker every 30 minutes for five hours (or until the pellets had disintegrated). After dilution, the concentration of OTC. in the water samples was determined by high performance liquid chromatography ("HPLC"). HPLC. readings were taken by adding 2.00 ml samples to 4.00 ml of methanol. The seawater/methanol mixture was placed in a freezer for ten minutes, and thereafter centrifuged for an additional ten minutes. The resulting solution was injected directly into the HPLC. apparatus, comprising a C8-Brownlee, Spheri-5, MPLC. (10 cm × 4.6 mm, 3 cm × 4.6 mm) column; a $C_{18}$-Corsail 37–50μ precolumn, mobile phase 0.02 M oxalic acid (pH 2), acetonitrile 800/120 (v/v) +5% dimethylformamide. OTC. was detected at 280 nm, using a liquid velocity of 1.0 ml/min, with 10μ injection (automatic at 20° C.). The present OTC. dissolved in the water versus time was determined from the mean of the six units tested. The data is shown in FIGS. 2 and 3.

FIGS. 2 and 3 show that OTC. was released from the prior art products A and B. There was no substantial release from the dosage form of the invention under the same conditions. An increase in temperature did not materially affect the release of active agent from the dosage form of the invention.

The disintegration time of the pellets was also determined, by measuring the time it took for the seawater-immersed pellets to pass through a 2 millimeter diameter bottom sieve, or the time required before the pellets became completely fragmented. The disintegration time was calculated as a mean from six measurements. The data is presented in Table 1, for 4° and 18° C. seawater immersion, respectively.

TABLE 1

| Product | Disintegration Time (hrs.) | |
|---|---|---|
| | 4° C. | 18° C. |
| "AQUAPHARMAKA" | >5 | >5 |
| Product A | 5* | 4.5 |
| Product B | 2.5 | 1.5 |

*The pellets were almost completely eroded and were very brittle.

* The pellets were almost completely eroded and were very brittle.

Table 1 shows that the dosage form of the invention remains stable for more than 5 hours, and did not disintegrate.

EXAMPLE 2

Active Agent Release Studies—

Flumecuine and Oxolinic Acid

The procedure of Example 1 was repeated in order to compare the release of a flumequine-containing "AQUAPHARMAKA" device according to the invention and, Product A containing oxolinic acid. Although the two tested dosage forms contain different medicines, both active agents dissolve in water, and the presence of one or both of these agents in the surrounding seawater would indicate leakage from the dosage form. The "AQUAPHARMAKA" pellets contained 0.4% flumequine. They were approximately 6 mm in size, and weighed approximately 0.25 grams each. The Product A pellets contained 0.5% oxolinic acid. They were 6 mm in size, and weighed approximately 0.37 grams each. The same apparatus and procedure of Example 1 was utilized, and the release of active agent from the pellets into the surrounding seawater was determined at 4° C. and 18° C. Seawater samples of 5 ml volume were withdrawn every 30 minutes for 5 hours, or until the pellets had disintegrated. The water samples withdrawn from the Product A-containing beaker (oxolinic acid) were diluted 1:1 with 0.01 N NaOH. The diluted samples were centrifuged at 4,000 rpm for 5 minutes. The water samples from both beakers were then centrifuged at 4,000 rpm for 5 minutes. The concentration of flumequine and oxolinic acid was measured by HPLC. as in Example 1. The results are set forth in FIG. 6 (4° C.) and FIG. 7 (18° C.).

Figure 6:
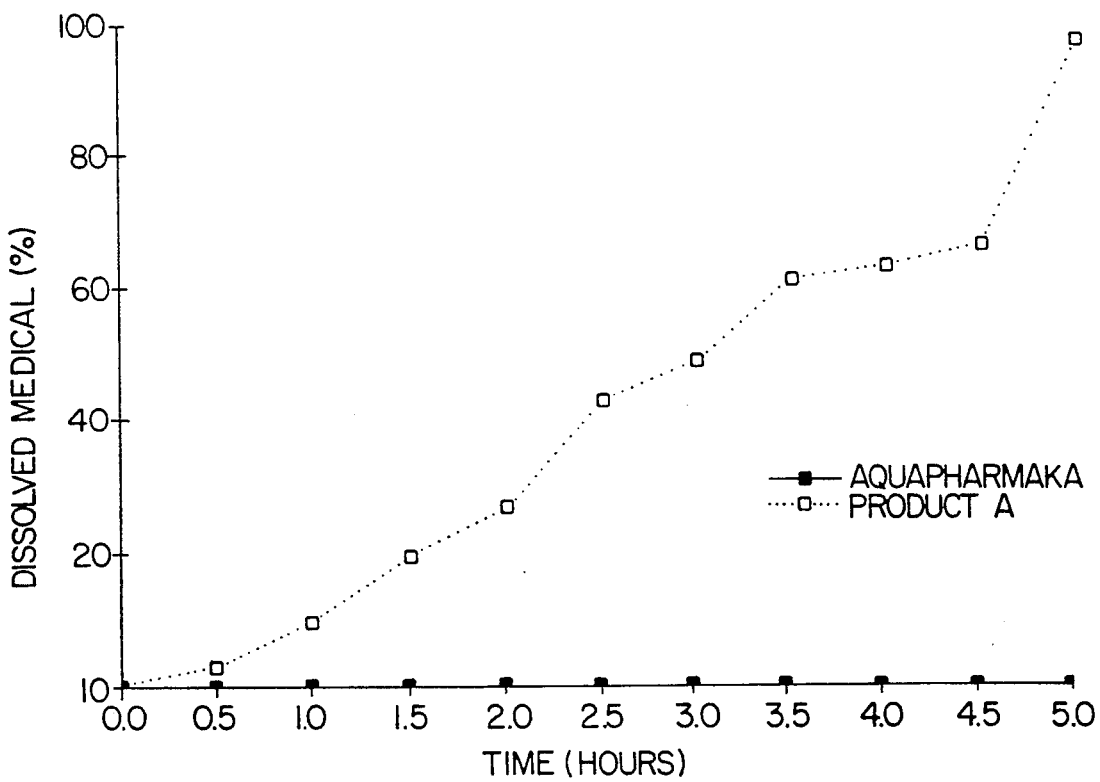
FIG. 6 compares the release rate of flumequine from the "AQUAPHARMAKA" dosage form (0.4% flumequine) and the release rate of oxolinic acid from Product A (0.5% oxolinic acid), at 4° C.
Figure 7:
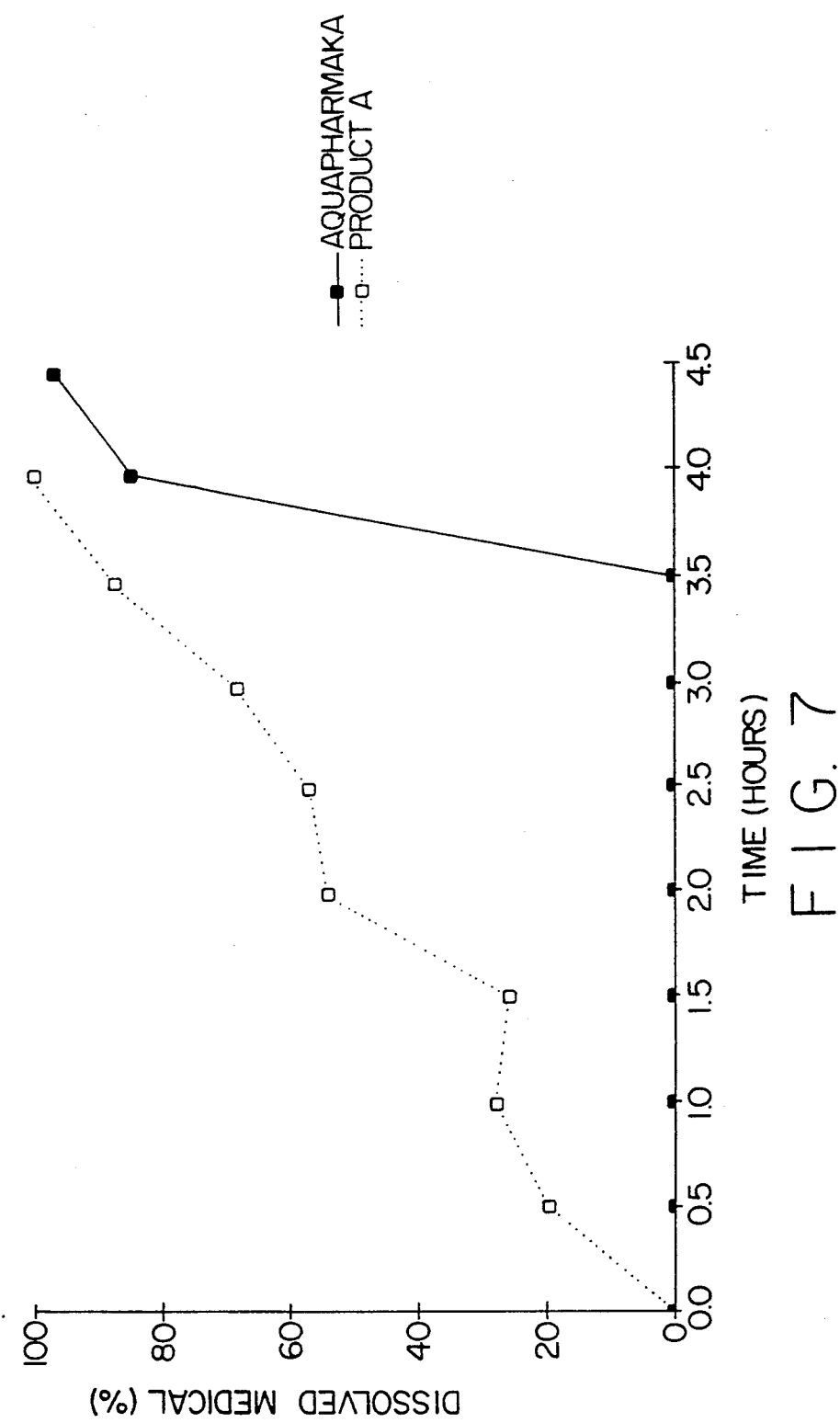
FIG. 7 compares the release rates of the same dosage forms as in FIG. 6, but at a water temperature of 18° C.

FIGS. 6 and 7 indicate that leakage of active agent from the "AQUAPHARMAKA" dosage form of the present invention is significantly slower than leakage of oxolinic acid from Product A. At 4° C., there was no sign of flumequine in the seawater surrounding the "AQUAPHARMAKA" dosage form, after 5 hours. At 18° C. the leakage of flumequine from the "AQUAPHARMAKA" pellets started at 3.5 hours. At 4.5 hours, 90% of the flumequine had dissolved into the seawater, and the pellets disintegrated.

On the other hand, dissolution of oxolinic acid from the pellets of Product A started immediately, both at 4° C. and 18° C. After 4 hours, 100% of the oxolinic acid from Product A dissolved into the surrounding seawater, and the pellet was completely eroded.

These results indicate that the "AQUAPHARMAKA" pellet according to the invention effectively prevents leakage of antibiotics to the surrounding medium far better than the commercially available Product A. The structure of the dosage form of the invention remains in tact for at least 3.5 hours in seawater between 4° C. and 8° C. This indicates that excess drug is removed from the dosage form only after several hours have elapsed after feeding. Contamination with the environment surrounding the fish farm is thus minimized.

It should be noted that while the "AQUAPHARMAKA" pellet of the invention and Product A contained different active ingredients in the above-described test (flumequine vs. oxolinic acid, respectively), both agents are similar antibiotics to the extent they display similar minimum inhibitory concentrations for various bacteria strains, as set forth in Table 2:

TABLE 2

| Bacterial Strain | Minimal Inhibitory Concentration | |
|---|---|---|
| | Flumequine | Oxolinic Acid |
| Vibrio salmonicidia | 0.035 | 0.07 |
| Vibrio anguillarum, serotype 1 | 0.035 | 0.035 |
| Yersinia ruckeri, serotype 2 | 1.2 | 1.0 |
| Yersinia ruckeri, serotype 3 | 0.25 | 0.25 |

EXAMPLE 3

Active Agent Utilization Studies—OTC

The absorption of active materials form the dosage form of the invention was compared to absorption of the active material form Products A and B. Absorption was determined by measuring the OTC concentration in plasma and muscle tissue from fish fed with "AQUAPHARMAKA" containing 1.2 wt.% OTC, Product A containing 1.0 wt.% OTC and Product B containing 1.2 wt.% OTC. Accordingly, fish were fed four times on day 0 with "AQUAPHARMAKA", Product A or Product B at a seawater temperature of 5°–7° C. Blood and tissue samples were collected at days 1, 2, 3, 4, 7, 14, 21 and 50. the samples were prepared and analyzed for OTC content according to the following protocols.

Determination of OTC muscle concentration. Minced fish tissue (10 mg muscle or 5 mg liver) was homogenized three times in 0.01 M phosphate buffer containing 0.1 M ethylenedinitrilotetraacetic disodium salt, pH 4.2. Fat was extracted by addition of a mixture of hexane and dichloromethane. Proteinaceous residues were precipitated by addition of solid natrium chloride, followed by heating to 48° C. and rapid cooling in a freezer. Following centrifugation, the extract was purified on a C8 solid-phase Sepralyte ® extraction column (Analytical International). OTC was eluted from the column with 5% water in acetone, and thereafter with 10% water in acetone. The acetone was evaporated by means of nitrogen. The residue was diluted int he mobile phase and analyzed by HPLC, utilizing demeclocycline as an internal standard for quantifying OTC.

Determination of OTC plasma concentration. Plasma samples (100–1000 μl) were treated with trifluoroacetic acid to precipitate plasma proteins. After heating to 37° C., the remaining solution was centrifuged and analyzed on HPCL as above.

Figure 4:
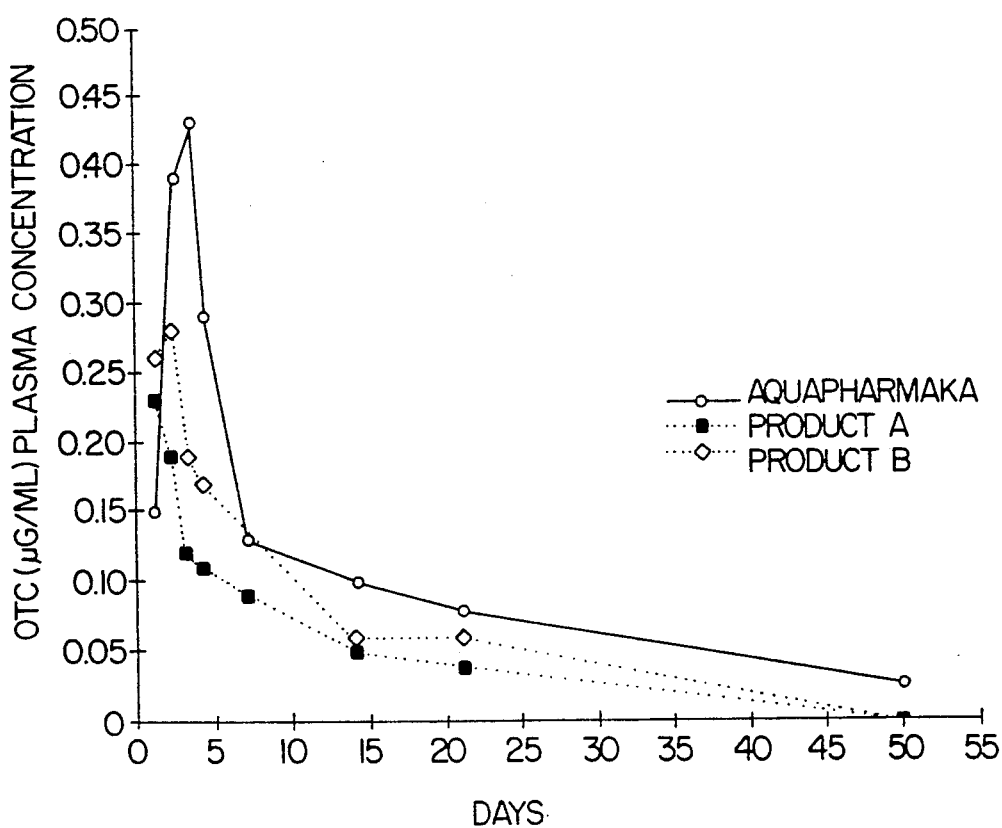
FIG. 4 compares the plasma concentration of OTC in fish fed the two commercially available medicated feed pellets and the "AQUAPHARMAKA" dosage form of the invention.
Figure 5:
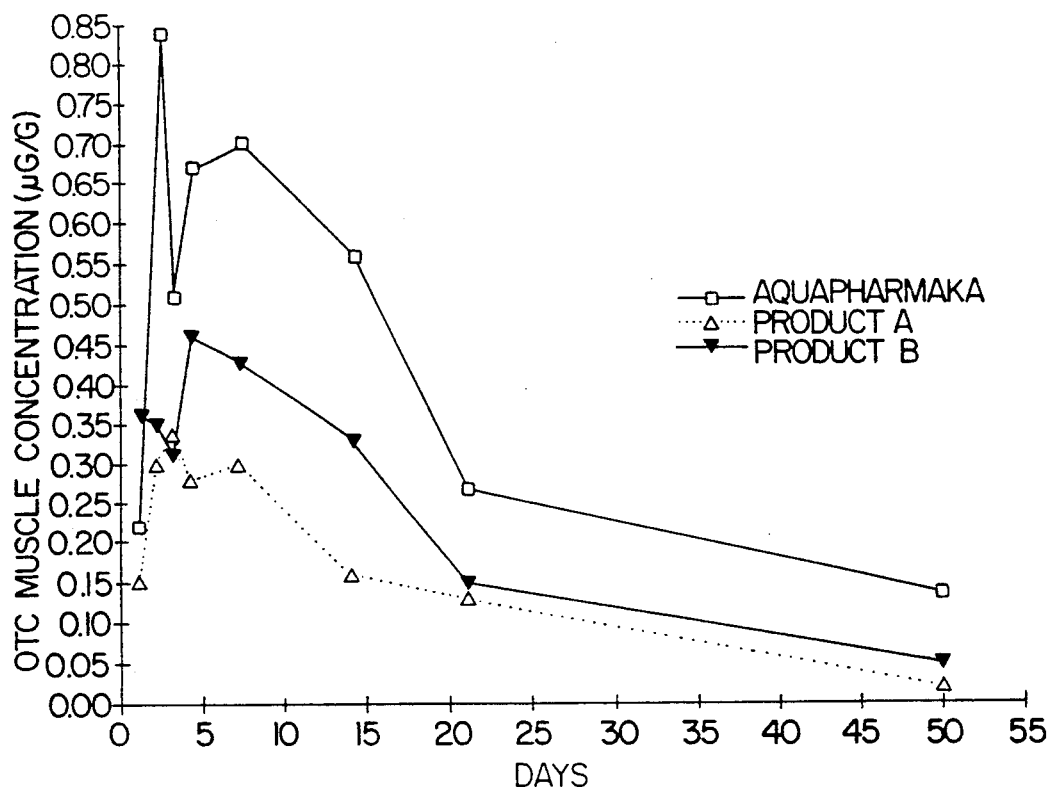
FIG. 5 compares the OTC. muscle concentration in fish fed the two commercially available medicated feed pellets and the "AQUAPHARMAKA" dosage form of the invention.

The results of the blood plasma and muscle tissue OTC determination are set forth in FIGS. 4 and 5, respectively. The maximum values of each measurement are additionally provided in Table 3.

TABLE 4

| Product | Amount of Product admin. (kg) | Period of treatment (days) | Total dose (g) | Dose (mg) per day/kg fish | Total dose (mg) per kg fish |
|---|---|---|---|---|---|
| "AQUAPHARMAKA" (0.2%) | 58 | 10 | 104 | 15 | 150 |
| "AQUAPHARMAKA" (0.5%) | 58 | 10 | 320 | 47 | 470 |
| "AQUAPHARMAKA" (0.5%) | 28 | 5 | 154 | 46 | 230 |
| Product A (0.5%) | 23 | 8 | 106 | 20 | 160 |

TABLE 3

| Product | Max. conc. in plasma μg/ml | Day | Max. conc. in muscle μg/ml | Day |
|---|---|---|---|---|
| "AQUAPHARMAKA" | 0.43 ± 0.04 | 3 | 0.84 ± 0.3 | 2 |
| Product A | 0.23 ± 0.03 | 1 | 0.34 ± 0.08 | 3 |
| Product B | 0.28 ± 0.04 | 2 | 0.46 ± 0.06 | 4 |

The plasma and muscle uptake tests indicate a superior degree of acceptance and absorption of active agent from the dosage form of the invention as compared with the test prior art products.

EXAMPLE 4

Active Agent Utilization Studies

Flumequine and Oxolinic Acid

Studies to determine the concentration of active agent in muscle resulting form the treatment of fish with "AQUAPHARMAKA" (containing flumequine) and Product A (containing oxolinic acid) were performed. "AQUAPHARMAKA" pellets containing 0.2% and 0.5% flumequine, by weight, respectively, were compared to pellets of Product A containing 0.5% oxolinic acid. The 0.2% "AQUAPHARMAKA" pellet was administered to one group of fish daily for 10 days at a feeding rate of 0.86%, based upon the weight of the fish. The 0.5% "AQUAPHARMAKA" pellet was administered similarly at a feeding rate of 0.86% for 5 days to one group of fish, and for 10 days to another group of fish. The Product A pellets, containing 0.5% oxolinic acid, were administered daily at a feeding rate of 0.43% for 8 days to yet another group. (The manufacturer of Product A pellets recommends a feeding rate of 0.20–0.50% for 10 days, according to the directions for use.) All pellets were fed by an automatic feeder. The output of the feeder was 20–50 pellets every 1 or 2 minutes for 8–12 hours per day, during the whole period of administration of medicinal pellets, the appetite was good in all groups of fish. At the end of the treatment period, the fish were transferred to an empty pen and fed growth feed.

The dosage information is summarized in Table 4.

Twelve fish on each pellet regimen were samples at day's end on the first day of administration of product and on day 2, 4, 7, 9, 12, 19, 26 and 41 after the start of product administration. Plasma and muscle samples were collected from each group. The blood samples (2–10 ml) were collected from the caudal vein. Plasma was isolated by centrifugation of the blood at 4,000 rpm for 10 minutes. Plasma and tissue samples (whole liver, filet from one side of the fish, and kidney) were immediately frozen and stored at −70° C. until analyzed. All plasma samples and four muscle samples were selected from fish with plasma values around the median from each group.

Determination of Active Agent Plasma Concentration

The amount of flumequine or oxolinic acid in the fish plasma was determined as follows. The plasma samples were cleaned by solid phase extraction. C2 Bond Elut TM columns were conditioned with methanol and phosphoric acid (1M) prior to application of 250 μl plasma and internal standard. Oxolinic acid was used as the internal standard when the analyte was flumequine, and vice versa. After washing the columns with water and phosphoric acid (1M) the analyte and internal standard were eluted with 1250 μl acetonitrile-methanol-1M phosphoric acid (80:10:10). The eluates were analyzed by HPLC using a column packed with polystyrene divinylbenzene (PLPR-S, 5 μm), and by fluorescence detection (emission: 380 nm, excitation: 262 nm). the mobile phase was acetonitriletetrahydrofuran -0.002M phosphoric acid (20:15:65) at a flow rate of 0.7 ml/min.

Determination of Active Agent Muscle Concentration muscle samples (10–20 gl) were ground and blended with a mixture of 3 ml NaOH (1M) and 20 ml acetone. The internal standard was added as in the analysis of the plasma samples. After centrifugation, the homogenization was repeated twice. Acidified, collected supernatants were extracted with chloroform. The chloroform was evaporated to a small volume. Further clean-up was carried out by liquid-liquid extraction between chloroform and acidic/basic aqueous solutions. The chloroform solution was evaporated to dryness and the dry residue was dissolved in the mobile phase. HPLC-analysis was performed, as was carried out on the plasma samples.

Figure 8:
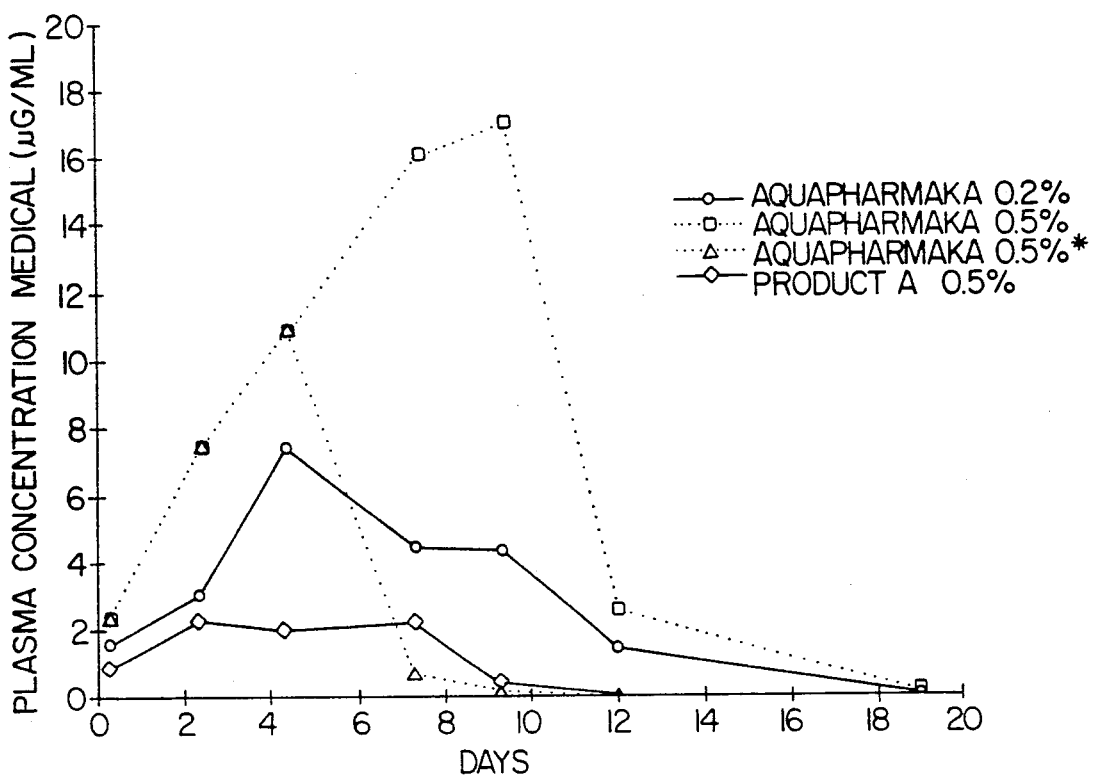
FIG. 8 compares the plasma concentration of active agent in fish fed "AQUAPHARMAKA" containing 0.2%, 0.5% (ten day feeding), 0.5%* (five day feeding) and Product A containing 0.5% oxolinic acid.
Figure 9:
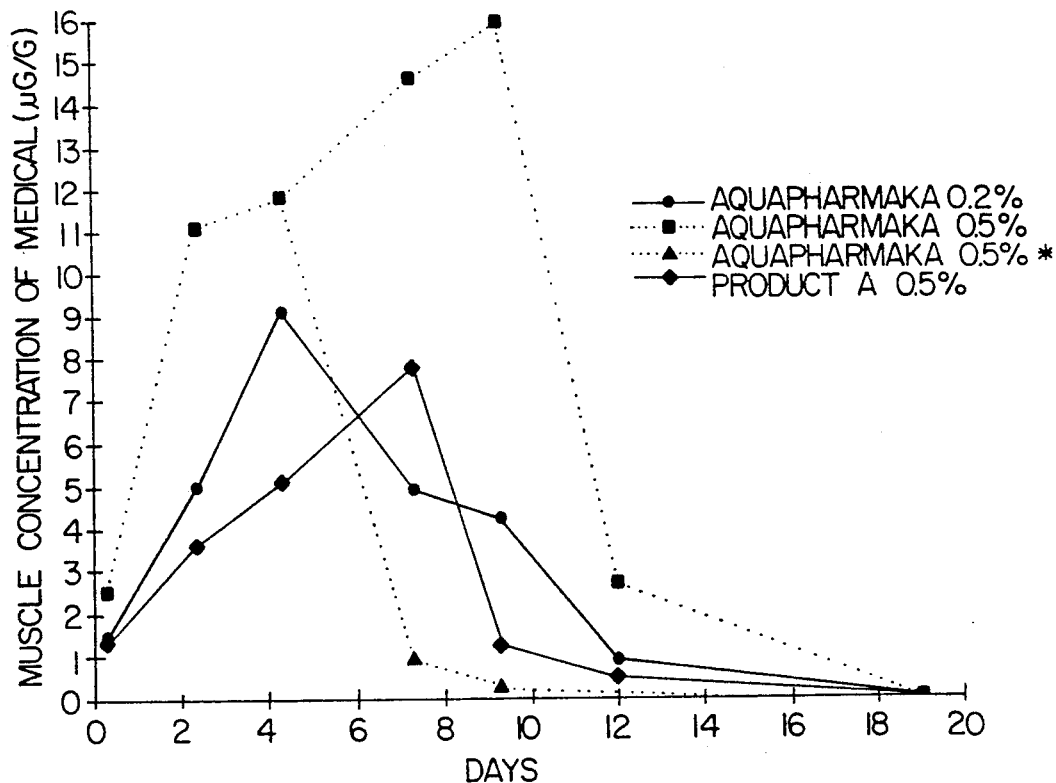
FIG. 9 compares the active agent muscle concentration in fish fed the same dosage forms as in FIG. 8.

A total of 342 plasma samples and 134 muscle samples were analyze din this manner. Curves for the mean concentration of flumequine or oxolinic acid in plasma are shown in FIG. 8. Curves for the mean concentration of flumequine or oxolinic acid in muscle are shown in FIG. 9. The curves marked "AQUAPHARMAKA 0.5% " resulted from a ten day treatment period. The curves marked "AQUAPHARMAKA 0.5%*" resulted from a five day treatment period.

The data in Tables 3 and 4 and FIGS. 4, 5, 8 and 9, reflecting a large scale experiment wherein medicinal pellets were administered to a large salmon population, confirms the favorable absorption properties of active agent from dosage forms according to the invention. Specifically, it is possible to achieve a high flumequine concentration in fish through the dosage form of the present invention, as early as the first day of medication.

The extent of bioavailability of flumequine and oxolinic acid from the dosage forms tested is estimated by consideration of the area under the curves ("AUC") in FIGS. 8 and 9. When comparing the area under the curve per dosage values, as summarized in Table 5 below, it is apparent that the bioavailability of active agent, based upon the plasma results, is 3.5 times greater for flumequine in the "AQUAPHARMAKA" 0.2% pellets than for oxolinic acid in the Product A medicated feed. For the muscle data, the bioavailability is 1.4 times better for flumequine in the dosage form of the invention, than for oxolinic acid in the Product A pellets.

TABLE 5

| Product | PLASMA | | MUSCLE | |
|---|---|---|---|---|
| | AUC ($\mu$g day/ml) | AUC/total dose/kg fish | AUC ($\mu$g day/ml) | AUC/total dose/kg fish |
| "AQUAPHARMAKA" (0.2%) | 57 | 0.38 | 60 | 0.40 |
| "AQUAPHARMAKA" (0.5%) 10 day feeding | 142 | 0.30 | 140 | 0.29 |
| "AQUAPHARMAKA" (0.5%) 5 day feeding | 47 | 0.20 | 57 | 0.25 |
| Product A (0.5%) | 17 | 0.11 | 45 | 0.28 |

EXAMPLE 5

Clinical Studies

The "AQUAPHARMAKA" dosage form according to the present invention, containing flumequine as the active drug, or Product A containing oxolinic acid, was administered to Atlantic salmon (Salmo salar) weighing 120–500 grams. The fish were maintained in fiberglass tanks (0.5–8.5 m$^3$) containing circulating seawater. The fish were experimentally infected with a bacteria suspension by intraperitoneal injection with 0.1 ml of a challenge inoculum. The inoculum density was predetermined form pilot experiments to give mortalities within calculated criteria. Before challenge, the fish were anesthetized in 30% chlorobutanol diluted 1:1000. Thereafter, the fish, were medicated three times a day at regular intervals. The water temperature was measured daily. The appetite of the fish, and the number of dead fish were recorded daily for the duration of the test. The test groups were administered either "AQUAPHARMAKA" pellets according to the invention containing flumequine, or Product A medicated feed containing oxolinic acid. All mortalities in the medicated groups were screened for specific disease. The cause of mortality was recorded as specific or non-specific. The results of the experiments are summarized below.

EXPERIMENT 1

In this experiment, the Atlantic salmon were infected with Yersinia ruckeri. One day after challenge with the bacterial inoculum, the test groups were administered either "AQUAPHARMAKA" 0.4% or Product A medicated feed 0.5% for ten days. The dosage was 20 mg of drug/kg/day. Both drugs were effective in controlling yersiniosis at challenge doses of 10$^8$ cells per mol. Twenty days after the start of medication, the mortality was 22% in the group administered "AQUAPHARMAKA" 0.4%, and 30% in the group given Product A medicated feed 0.5%. The control group (no medication) displayed a mortality of 48%. No difference in the mortality between the drugs was observed until day ten of medication. In the period between day ten and day twenty after the start of medication, the mortality was 8% less in the "AQUAPHARMAKA" group. The result may indicate that the "AQUAPHARMAKA" dosage form according to the invention is able to stop the outbreak of yersiniosis at an earlier development stage than the Product A medicated feed.

EXPERIMENT 2

In this experiment, medication was started three days prior to challenge with the Yersinia ruckeri. The medication lasted a total of ten days, that is, for three days prior to challenge with the inoculum, and seven days thereafter. The dosage of flumequine ("AQUAPHARMAKA" 0.4%) and oxolinic acid (Product A medicated feed 0.5%) was 20 mg/kg/day. By beginning the medication prior to infection, the acceptance of the pellets was optimal. No mortality was observed in the group administered the dosage form according to the invention, while a 15% mortality occurred in the group which received Product A. The mortality in the control group was 100%.

EXPERIMENT 3

In this experiment, the prophylactic effect of "AQUAPHARMAKA" 0.4% and "AQUAPHARMAKA" 0.5% was compared with Product A medicated feed at 0.5%. All drugs were administered prior to challenge with Yersinia ruckeri. No mortality was observed upon administration of 50 mg flumequine/kg as "AQUAPHARMAKA" 0.5% one day prior to challenge with bacterial inoculum. Mortality in the control group was 96%. The corresponding dosage of oxolinic acid (60 mg/kg) as Product A resulted in 6% mortality. The optimal affect was achieved by a single flumequine dosage of 50 mg/kg, as compared to two separate 20 mg/kg doses. Thus, 50 mg flumequine/kg is a suitable dosage for treatment of yersiniosis.

The above results indicate that the dosage form of the present invention provides better results than commercially available medicated fish feeds in the therapeutic and prophylactic treatment of fish diseases. These results evidence the superior acceptance of the dosage form of the present invention by feeding fish, and the superior absorption of the active compound from the dosage form, over the commercially available pellets.

Fish may be effectively medicated by administering to the fish, for ingestion, the pharmaceutical dosage form according to the invention. The dosage form is particularly preferred in administering medicament to the members of the class Salmoniformes.

The present invention may be embodied in other specific forms without departing from the spirit or essential attributes thereof and, accordingly, reference should be made to the appended claims, rather than to the foregoing specification, as indicating the scope of the invention.

We claim:

1. A pharmaceutical dosage form for the oral administration of at least one biologically active agent to fish by ingestion comprising:
   (a) an outer layer of a coating material, wherein said coating material comprises:
      (i) fish meal,
      (ii) an aqueous extract from edible marine material, and
      (iii) water; and
   (b) at least one internal chamber defined by said outside layer suitable for containing the biologically active agent,
wherein said outer layer is substantially impermeable to water and to the biologically active agent contained within the internal chamber.

2. A pharmaceutical dosage form according to claim 1 wherein said aqueous extract from marine material comprises aqueous extracts from marine materials selected from the group consisting of herring, blue whiting, octopus waste, fish waste, shrimp waste, krill and the aqueous press water which is a by-product of the production of fish meal.

3. A pharmaceutical dosage form according to claim 2 wherein the outer layer further contains a binder comprising from about 5% to about 20%, by weight of the dosage form.

4. A pharmaceutical dosage form according to claim 3 wherein the binder comprises about 10% of the dosage form, by weight.

5. A pharmaceutical dosage form according to claim 1 wherein the chamber contains a carrier material for the active agent, which carrier material is coextrudable with the outer layer.

6. A pharmaceutical dosage form according to claim 5 wherein the carrier material comprises an extrudable medium which solidifies at a temperature below about 0° C.

7. A pharmaceutical dosage form according to claim 5 wherein the carrier comprises an aqueous gel forming material.

8. A pharmaceutical dosage form according to claim 1 wherein said coating material further comprises a vegetable material suitable for forming said outer layer.

9. A pharmaceutical dosage form according to claim 8 wherein said vegetable material comprises at least one component selected from the group consisting essentially of: soy meal, potato starch and starch derivatives, wheat flour, lactose, and the like.

10. A pharmaceutical dosage form according to claim 1 wherein said outer layer further comprises a binder.

11. A pharmaceutical dosage form according to claim 10 wherein said binder comprises a modified starch derivative.

12. A pharmaceutical dosage form according to claim 11 wherein said modified starch derivative comprises a modified hydroxypropyl-distarch phosphate.

* * * * *